(12) United States Patent
Slotznick et al.

(10) Patent No.: US 11,278,438 B2
(45) Date of Patent: Mar. 22, 2022

(54) CUSHION FOR ORTHOPEDIC CASTS

(71) Applicants: Benjamin Slotznick, Mt. Gretna, PA (US); Roy Niedermayer, Bethesda, MD (US)

(72) Inventors: Benjamin Slotznick, Mt. Gretna, PA (US); Roy Niedermayer, Bethesda, MD (US)

( * ) Notice: Subject to any disclaimer, the term of this patent is extended or adjusted under 35 U.S.C. 154(b) by 405 days.

(21) Appl. No.: 16/102,853

(22) Filed: Aug. 14, 2018

(65) Prior Publication Data
US 2019/0053932 A1 Feb. 21, 2019

Related U.S. Application Data

(60) Provisional application No. 62/615,514, filed on Jan. 10, 2018, provisional application No. 62/547,210, filed on Aug. 18, 2017.

(51) Int. Cl.
| | |
|---|---|
| *A61F 5/01* | (2006.01) |
| *A61F 5/10* | (2006.01) |
| *A61F 5/37* | (2006.01) |
| *A61F 13/04* | (2006.01) |
| *A61F 5/30* | (2006.01) |

(52) U.S. Cl.
CPC .......... *A61F 5/0118* (2013.01); *A61F 13/041* (2013.01); *A61F 5/30* (2013.01)

(58) Field of Classification Search
CPC ........ A61F 5/30; A61F 5/0118; A61F 13/041; A61F 13/069; A61F 5/05866; A61F 5/05875
See application file for complete search history.

(56) References Cited

U.S. PATENT DOCUMENTS

| | | | |
|---|---|---|---|
| 4,479,490 A * | 10/1984 | Dedo | A61F 13/041 602/11 |
| 4,530,351 A | 7/1985 | Gordon | |
| 4,532,922 A * | 8/1985 | Golyakhovsky | A61F 13/041 602/11 |
| 5,180,359 A | 1/1993 | Dedo | |
| 5,561,856 A * | 10/1996 | Pesco | A41D 19/01588 2/16 |
| 5,916,184 A | 6/1999 | McKeel | |
| 6,695,801 B1 * | 2/2004 | Toronto | A61F 5/01 602/6 |
| 10,645,984 B2 * | 5/2020 | Hull | A41D 19/0006 |

(Continued)

*Primary Examiner* — Camtu T Nguyen
(74) *Attorney, Agent, or Firm* — Panitch Schwarze Belisario & Nadel LLP

(57) ABSTRACT

A cushion for use with orthopedic casts for encasing wrists, forearms and/or hands, when a finger, such as the thumb, is not itself encased in the cast, is provided. The cushion is manufactured from a moisture-proof, non-absorbent, closed-cell synthetic material, in the shape of a portion of a section of a hollow tube, so that when the cushion is placed against a flat surface, an inner surface of the cushion encloses a cavity or an empty space open at one end of the cushion. When the supplemental cushion is in use, the webbing that connects the human thumb and index finger is positioned in that empty space, and more particularly encased within the empty space of the cushion, so that chaffing and injury to that webbing during thumb movement and extension are minimized, while the wrist, forearm and/or hand are encased in the cast.

22 Claims, 15 Drawing Sheets

(56) References Cited

U.S. PATENT DOCUMENTS

2004/0002671 A1* 1/2004 Reaux .................... A61F 13/04
602/5
2007/0073201 A1* 3/2007 Campagna ............ A61F 13/041
602/8
2018/0177642 A1* 6/2018 Anderson ............... A61F 13/04

* cited by examiner

CUSHION FOR ORTHOPEDIC CASTS

CROSS-REFERENCE TO RELATED APPLICATIONS

This application claims priority to U.S. Provisional Patent Application No. 62/547,210, filed on Aug. 18, 2017, entitled "A Supplemental Cushion for Orthopedic Casts," and U.S. Provisional Patent Application No. 62/615,514, filed on Jan. 10, 2018, entitled "A Supplemental Cushion for Orthopedic Casts," the entire contents of which are incorporated by reference herein.

BACKGROUND OF THE INVENTION

The present invention relates to the field of orthotic or orthopedic device liners, that is, cushioning devices for orthopedic casts, and more specifically a device and method for using a supplemental cushion to prevent chaffing and injury to the webbing that connects the thumb and index finger (sometimes called the thenar space, and referred to herein as such), when the wrist or hand is encased in a cast but the thumb is not.

Casts are typically used to immobilize limbs and joints to permit healing of broken bones, or of surgically repaired muscles and tendons. Typically, the limb is first wrapped or encased in a material that cushions the limb from chaffing during the lengthy time that the cast is worn. The cushion or pad is then encased in a sheath or shell (the terms being used interchangeably herein), which provides rigidity and stability, in order to form the finished cast. Historically, the cushioning material was fabric or cotton padding, while the sheaths were made from plaster bandages, such as cotton impregnated with plaster of Paris which hardens after wetting. More recently, synthetic materials are used for both cushioning and sheaths. Examples include knitted fiberglass bandages impregnated with polyurethane, or bandages of thermoplastic. See, for example, U.S. Pat. No. 5,916,184, the entire contents of which are incorporated herein by reference.

When the wrist and hand are encased in part of the cast, the thumb and fingers are often not encased in the circumstance where they do not have to be immobilized, even if the cast itself must encase the palm of the hand in order to anchor the cast to the limb. Allowing freedom of movement of thumb and/or fingers allows the patient to more easily accomplish tasks of daily living during the long recuperation period.

However, the sheath material takes some time to set and harden, and the limb, along with encased bones, muscles and tendons, must not move during that time. Thus, even if a thumb is not encased, the thumb may be held at rest (and not moving) during the application of the sheath.

However, after the sheath has set, when a thumb is raised, the thenar space (i.e., the skin webbing between the thumb and forefinger) expands and extends beyond the plane of the palm. In contrast, when the thumb is at rest, it does not. This movement of the thenar space will rub against the cushion and sheath, producing chaffing and irritation, possibly even laceration, abrasion or maceration. This movement may also cause pain and discomfort.

Examples of previous attempts to reduce this type of abrasion are disclosed in U.S. Pat. Nos. 4,530,351 and 5,180,359. U.S. Pat. No. 4,530,351 eliminates the part of the sheath which encases the palm and the back of the hand, and instead keeps the sheath from sliding up the patient's arm with a smooth metal or plastic rod that is attached to the sheath. The rod crosses the palm, loops over the thenar space and the thumb and then continues over the back of the hand, connecting back to the sheath. The rod maintains contact with the thenar space via its smooth surface (rather than an abrasive one), and also keeps the contact to a minimum. However, similar to replacing the back-strap of a sandal with a metal rod that curves around the heel, such a metal rod would still allow for the risk of significant abrasion. In addition, the rod of U.S. Pat. No. 4,530,351 does not alleviate abrasions that may occur when medical personnel elect to anchor the sheath by encasing the palm and thenar space within the sheath material, as is frequently done.

U.S. Pat. No. 5,180,359 teaches how a padding with a raised edge can be placed on top of a stockinette/bandage casing before applying the sheath material, in order to ensure that the edges of the sheath material are not rough or inherently abrasive to skin that comes in contact with it. As such, the hole in the cast left for the thumb can have a smooth edge, as depicted in FIG. 28 and FIG. 29 of U.S. Pat. No. 5,180,359. However, this padding addresses only one cause of the abrasion, the rough edge of the sheath. This prior art padding does not alleviate abrasion from movement of the skin continually moving back and forth under tension at an edge (i.e., as the thumb moves up and down, expanding the web of the thenar space), because the hardened sheath material is still tight to the palm and thenar space.

Accordingly, there is a need for a cushion or padding that will allow for a sheath to be applied in customary manner, as known to medical professionals and practitioners of the art, while the thumb is at rest, and yet still provide room for the thenar space to expand when the thumb is extended, thereby alleviating pain and suffering of the patient during the healing period.

BRIEF SUMMARY OF THE INVENTION

The present invention is directed to a small supplemental cushion constructed of synthetic materials, with enough structural integrity to retain its general shape, but still configured to be squeezed for additional cushioning effect. The synthetic materials are preferably moisture and air impermeable, and more preferably water and air impermeable. The construction makes them non-absorbent and they may incorporate anti-microbial materials. The cushion is shaped and sized to provide a space between the palm and the central part of the cushion, into which the webbing between the thumb and forefinger can expand when the thumb is extended or raised.

In use, the supplemental cushion is placed over the thenar space with the thumb extended. Typical cushioning or padding is applied to the limb (e.g., hand, wrist, and arm), such as by wrapping the cushioning/padding around the palm of the hand, including wrapping it around the supplemental cushion so that the supplemental cushion is held in place next to the thenar space. After the typical cushioning is applied to the limb, the thumb can be relaxed. This supplemental cushion has sufficient structural integrity that when held in place by typical cushioning, the space for the thumb-forefinger webbing is not crushed. The sheath is then applied, and allowed to harden and set, in order to form the cast. After the sheath is hardened, the supplemental cushion will reduce chaffing of thenar space while the cast is worn.

These and other objectives and features of the present invention will be better understood and appreciated from the following detailed description of the main embodiment thereof, selected for purposes of illustration and depicted in the accompany drawings.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

DETAILED DESCRIPTION OF THE INVENTION

Figure 1A:
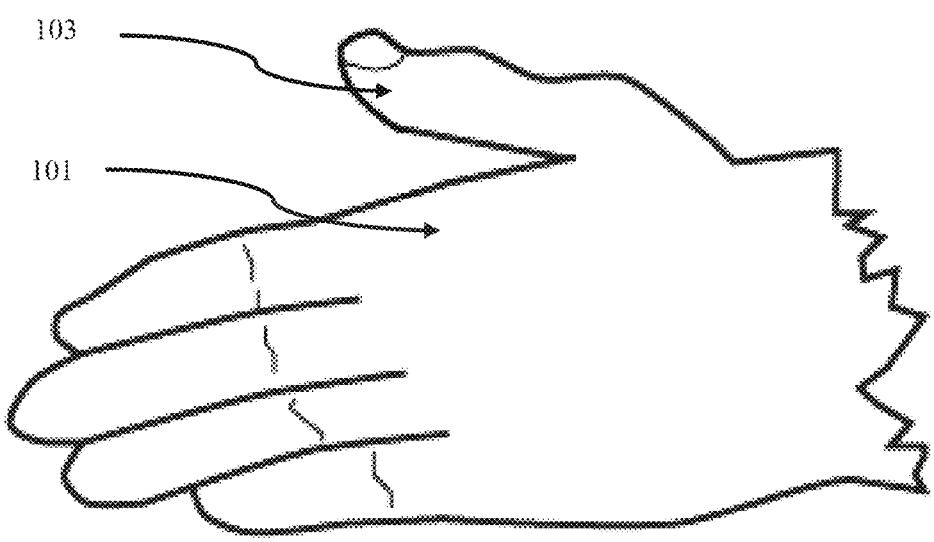
FIG. 1A shows a right hand with the thumb relaxed.

Reference will now be made in detail to the present embodiments of the invention illustrated in the accompanying drawings. It should be noted that the drawings are in simplified form and are not drawn to precise scale. Certain terminology is used in the following description for convenience only and is not limiting. The words "right," "left," "top," "bottom" and "lower" designate directions in the drawings to which reference is made. The words "first," "second," "third" and "fourth" designate an order of operations in the drawings to which reference is made, but do not limit these steps to the exact order described. The words "inwardly" and "outwardly" refer to directions toward and away from, respectively, the geometric center of the assembly and designated parts thereof. Unless specifically set forth herein, the terms "a," "an" and "the" are not limited to one element, but instead should be read as meaning "at least one." The terminology includes the words noted above, derivatives thereof and words of similar import.

Figure 1B:
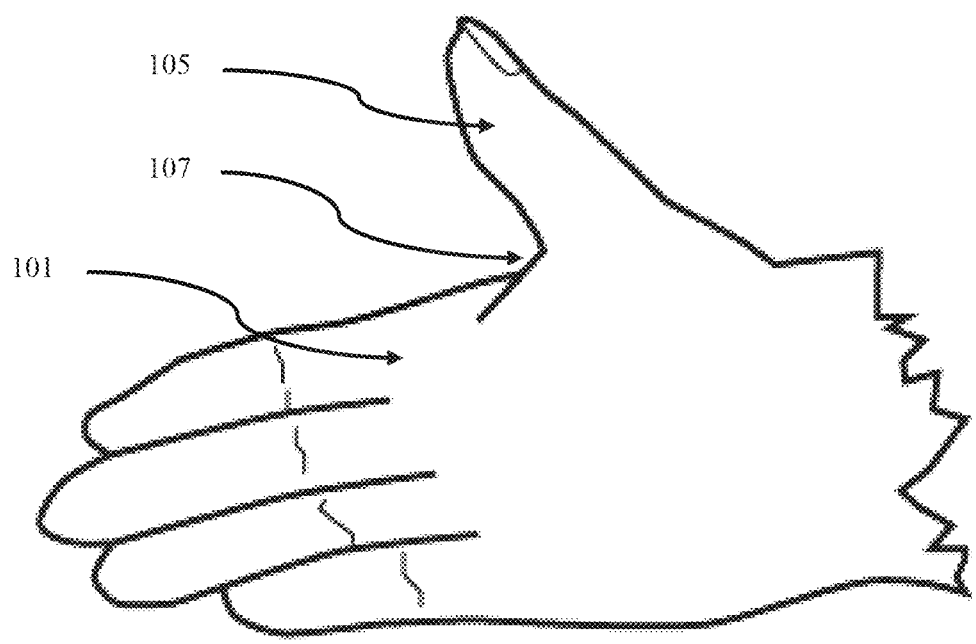
FIG. 1B shows a right hand with the thumb extended and the thenar space expanded.

Referring to FIG. 1A, there is depicted that when a thumb 103 is at rest in relationship to the hand/palm 101 to which it is attached, the webbing between the thumb and forefinger (i.e., thenar space) is not noticeable or prominent. In contrast, as depicted in FIG. 1B, when the thumb is extended as in 105, the thenar space 107 expands and extends beyond the surface of the palm 101.

Figure 2A:
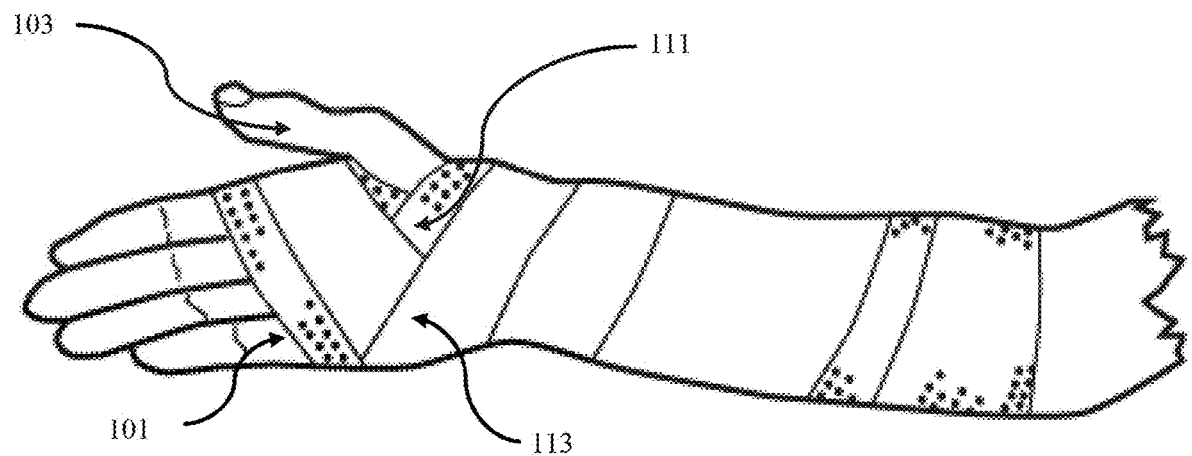
FIG. 2A shows a prior art wrist cast, with the cast being positioned on a right arm, wrist and palm with thumb relaxed.

Referring to FIG. 2A, there is depicted a cast with cushioning on the hand depicted in FIG. 1A. The thumb 103 is not extended. The palm, wrist and arm are first wrapped in a porous cushion or cast padding 111, depicted as the strips with the aeration indents (although not all aeration features are depicted.) An essential part of this cushioning or cast padding is that it needs to be very flexible, in order to allow enough to be wrapped around the limb.

Next, the sheath 113 is wrapped around the palm, wrist and arm. After that, the sheath is set and hardened by methods known to those proficient in the art. Hardening of the sheath varies depending up on the material of the sheath (e.g., cotton impregnated with plaster of Paris, fiberglass, thermoplastic and the like). As is the practice of those proficient in the art, the sheath does not cover all of the cushioning, but leaves some exposed, in order to prevent chaffing by the sheath of the skin at the edges of the sheath after it has hardened.

In some cases, as known to those skilled in the art, the medical practitioner will lift the exposed cushioning 111 up over the exposed edge of the sheath 113, and back over the top of the sheath 113. The cushioning 111 will then be attached to the sheath 113 during the process of sheath hardening (e.g., as the plaster, fiberglass or thermoplastic in the sheath hardens). This process is not depicted in FIG. 2A. The cushioning then protects the patient's skin from rubbing against the rough edge of the sheath.

Figure 2B:
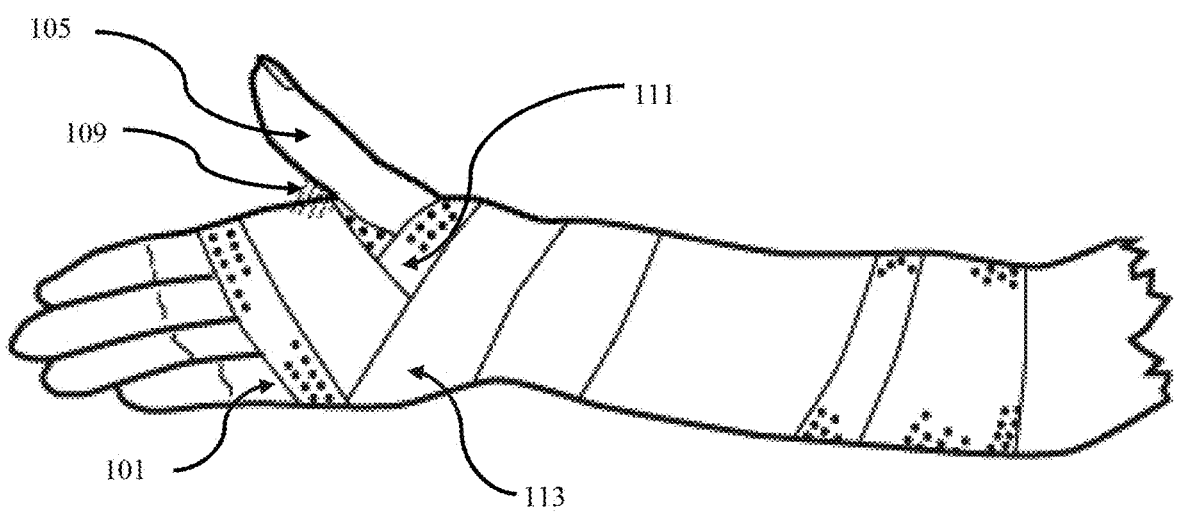
FIG. 2B shows a prior art wrist cast, with the cast being positioned on a right arm, wrist and palm with thumb extended, illustrating how the thenar space is pinched.
Figure 3A:
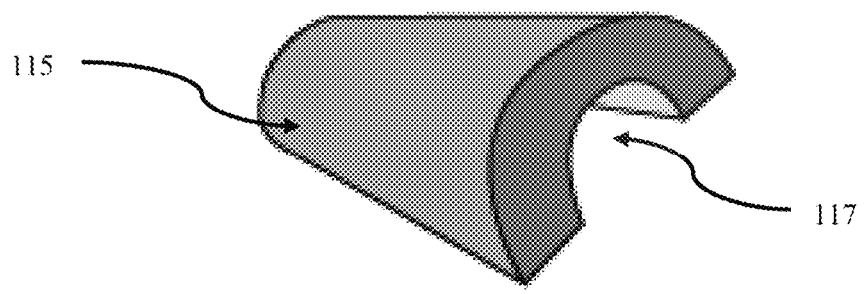
FIG. 3A is an orthogonal view of a cushion in accordance with an embodiment of the present invention.
Figure 3B:
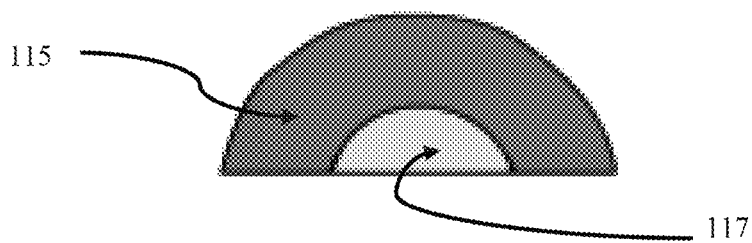
FIG. 3B is a front view of the cushion shown in FIG. 3A.
Figure 3C:
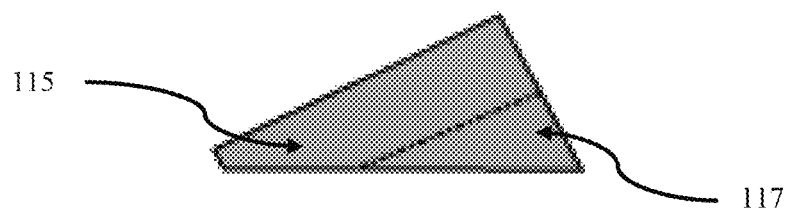
FIG. 3C is a side view of the cushion shown in FIG. 3A.
Figure 3D:
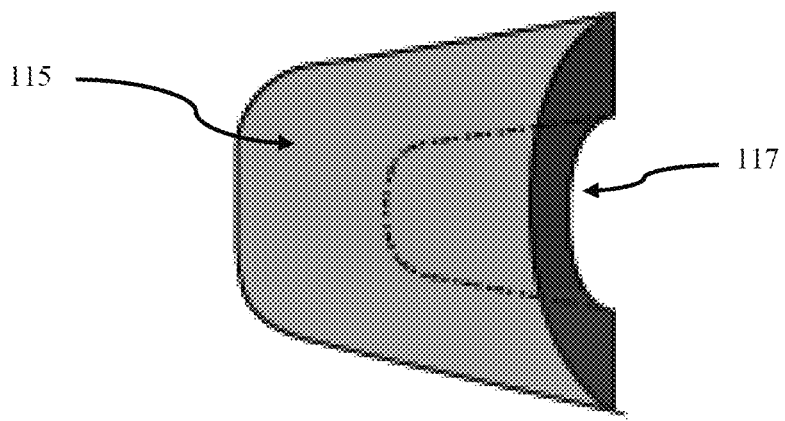
FIG. 3D is a top plan view of the cushion shown in FIG. 3A.

Consider next FIG. 2B, which shows the same cast on the same arm as FIG. 2A, but with the thumb 105 extended as in FIG. 1B. The thenar space is kept next to the palm 101 by the padding 111 and the outer sheath 113. The shaded space 109 is an area which would be occupied by the thumb-forefinger webbing (107 in FIG. 1B) if it were not pinched by the padding 111 and sheath 113. As the thumb is alternately relaxed (103 of FIG. 2A) and extended (105 of FIG. 2B), the skin on the thenar space will not only be pressed against the padding and sheath, but also rubbed back and forth against the edge of them, thereby injuring the skin of the webbing.

The purpose of the supplemental cushion of the present invention, depicted in FIGS. 3A-3D, is to create space within the cast and its padding to accommodate the thenar space, without compromising the structural integrity of the cast or typical methods of constructing it. A preferred embodiment of the supplemental cushion is made of a thermal foam closed cell polyethylene, which is both waterproof and non-absorbent. An alternative embodiment may use flexible elastomeric foam. In an alternative embodiment, an exterior skin adds an additional moisture (preferably water) and vapor barrier. In an alternative embodiment, anti-microbial materials are incorporated in the supplemental cushion of the present invention. Alternate embodiments of the supplemental cushion of the present invention use other materials with similar properties as known to those skilled in the art.

The foam is formulated so that it has a consistency similar to that used for pipe insulation for home water supply pipes, such as, but not limited to, Armaflex pipe insulation manufactured by the Armacell Company. The material can be easily compressed by a person's fingers squeezing it, but it retains its shape when wrapped. It will be understood by those skilled in the art that any material of similar compressibility properties may be used.

Figure 6A:
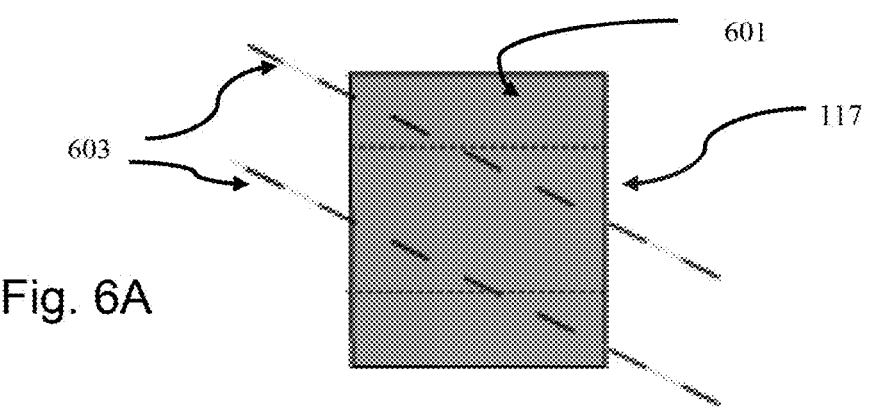
FIG. 6A shows a tube of closed cell polyethylene from which two cushions according to an embodiment of the present invention can be manufactured.
Figure 6B:
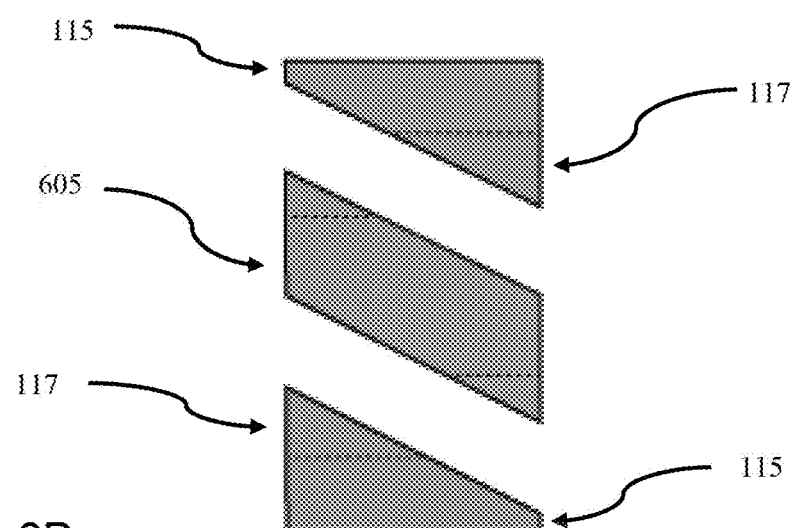
FIG. 6B demonstrates how two cushions according to an embodiment of the present invention are manufactured from the tube shown in FIG. 6A.
Figure 7A:
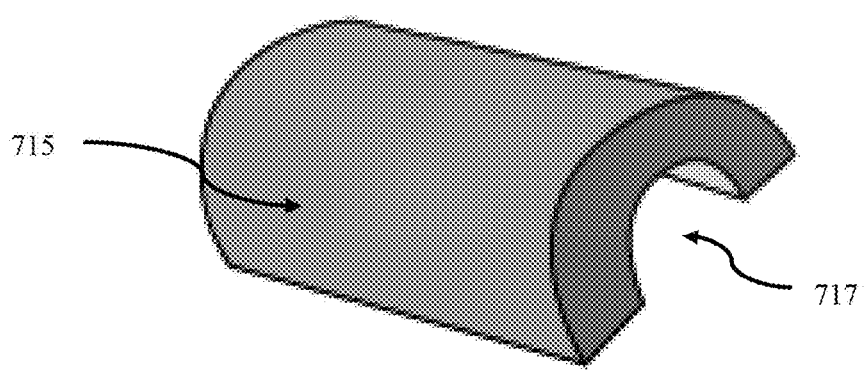
FIG. 7A is an orthogonal view of a cushion in accordance with another embodiment of the present invention.
Figure 7B:
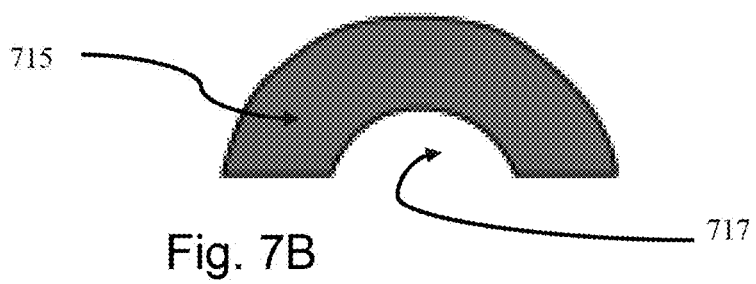
FIG. 7B is a front view of the cushion shown in FIG. 7A.
Figure 7C:
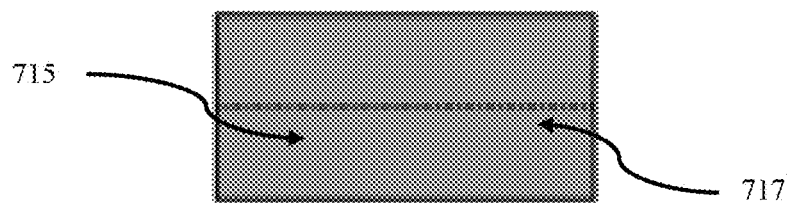
FIG. 7C is a side view of the cushion shown in FIG. 7A.
Figure 7D:
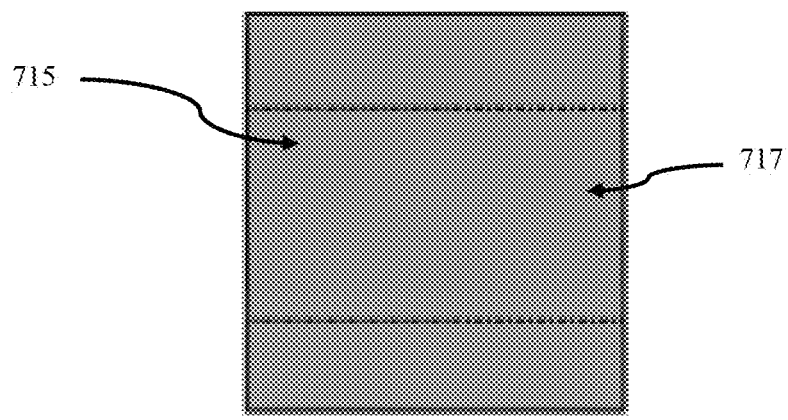
FIG. 7D is a top plan view of the cushion shown in FIG. 7A.
Figure 8A:
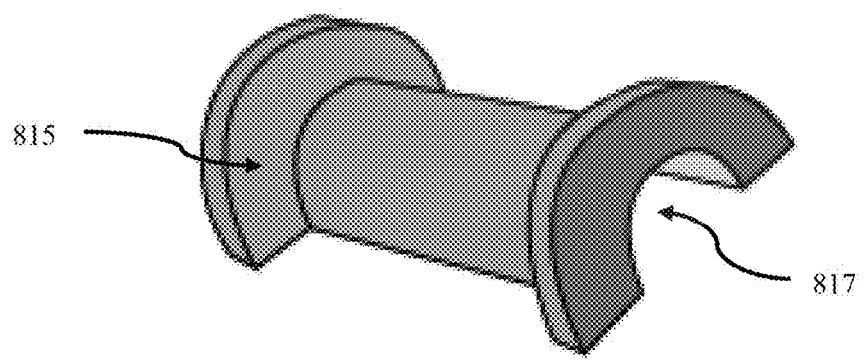
FIG. 8A is an orthogonal view of a cushion in accordance with another embodiment of the present invention.
Figure 8B:
FIG. 8B is a front view of the cushion shown in FIG. 8A.
Figure 8C:
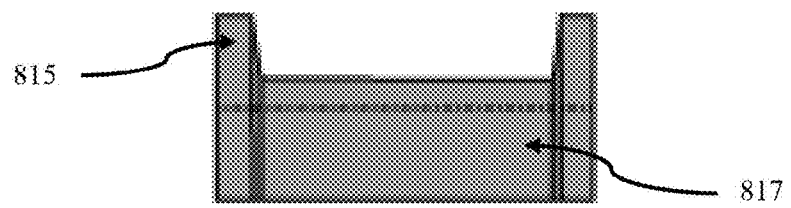
FIG. 8C is a side view of the cushion shown in FIG. 8A.
Figure 8D:
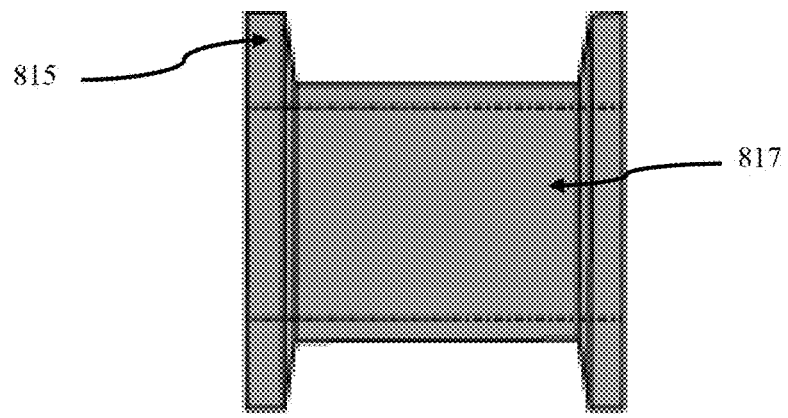
FIG. 8D is a top plan view of the cushion shown in FIG. 8A.

A preferred method of manufacturing the supplemental cushion starts with a hollow tube of the material 601, as depicted in FIGS. 6A-6B, with an outside diameter of approximately 1-½ inches, and an inside diameter of approximately ⅝". FIG. 6A shows such a tube and the cut-lines 603 for turning a 1-⅜" length of this tube into two (2) supplemental cushions, with the discarded material depicted as 605 (FIG. 6B). An alternative embodiment uses injection molding to form each individual cushion. Alternative embodiments use different construction methods as known to those skilled in the art.

Referring again to FIGS. 3A-3D, which show different views of a supplemental cushion (i.e., orthogonal, frontal, side and top), the cushion will sit flat on a planar surface, and provide a casing 115 around an open space 117 which can accommodate the thenar space. More particularly, the cushion comprises a body 115 having a first, outer surface and an opposing second, inner surface. In a first position, which is a pre-use position before the cushion is applied to a patient's hand, the inner surface defines a cavity 117 configured to receive the thenar space therein. Alternative embodiments of the casing 115 may be different sizes, different shapes, or have different cross-sections, as well as different shapes of the empty space or cavity 117. For example, the cavity 117 may be C-shaped, U-shaped, or triangular, rectangular or circular in cross-section. Preferably, the cavity 117 is C-shaped or U-shaped. In alternative embodiments, the supplemental cushion is manufactured in different sizes to fit different size hands, and with different compression characteristics.

In a preferred embodiment, the supplemental cushion is solid and has a smooth surface. In an alternative embodiment, the supplemental cushion has channels to promote airflow and liquid drainage. In an alternative embodiment, the supplemental cushion is pierced by one or more drainage holes and apertures.

In another alternative embodiment, the empty space 117 is filled with a softer, more flexible, less rigid cushioning material.

In an alternative embodiment, the supplemental cushion incorporates anti-fungal and/or anti-bacterial ingredients now known or to be later developed.

Figure 4A:
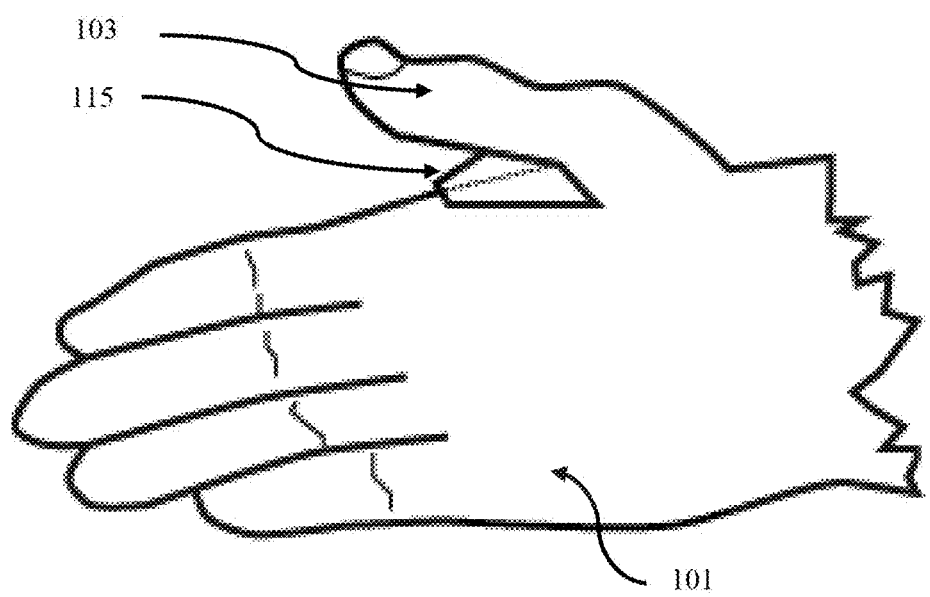
FIG. 4A illustrates the cushion shown in FIGS. 3A-3D positioned on the right hand of a patient with the thumb in a relaxed position.
Figure 4B:
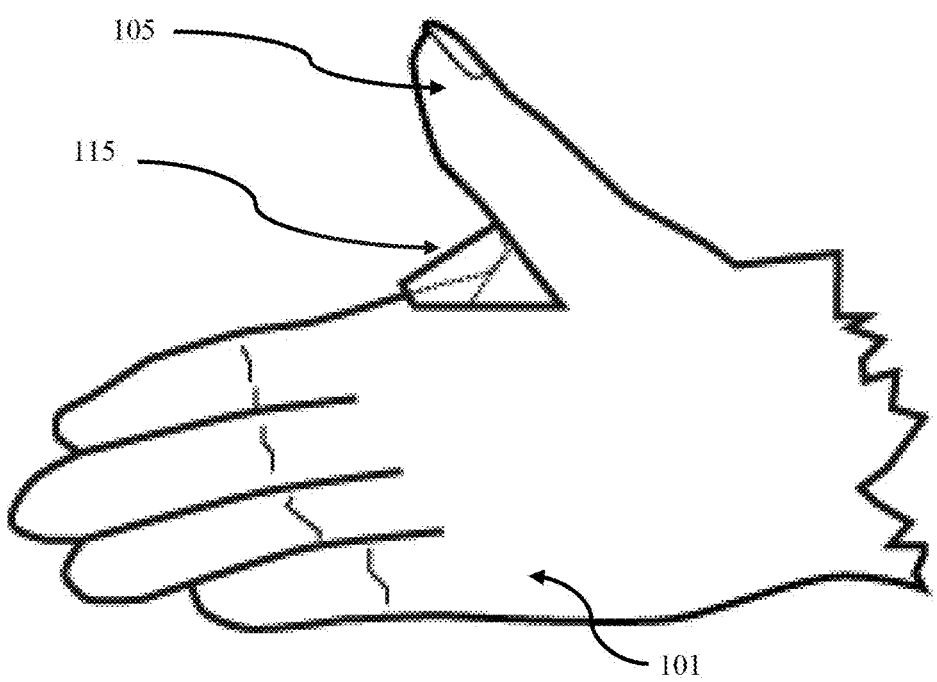
FIG. 4B illustrates the cushion shown in FIGS. 3A-3D positioned on the right hand of a patient with the thumb in an extended position.

FIG. 4B depicts how the supplemental cushion fits on a hand, particularly a right hand. The hand/palm 101 has an extended thumb 105, and the supplemental cushion 115 is placed over the thenar space. The dotted lines in FIG. 4B show the outline of the hand and thenar space covered by the supplemental cushion. Note that these dotted lines are depicted as solid lines in the respective portion of the thenar space and hand as depicted in FIG. 1B.

FIG. 4A shows how the supplemental cushion 115 appears on a hand 101 with the thumb in a relaxed position 103. In the relaxed thumb position, the thenar space is not expanded, and thus is not visible in the figure. Rather, the dotted lines in FIG. 4A show the outline of the hand that is covered by the supplemental cushion.

To apply the cast to the hand, the supplemental cushion 115 is first placed on the hand 101 as in FIG. 4B with the thumb extended. Then, a cushion or padding 111, as depicted in FIG. 5B, is begun to be wrapped around the hand 101 and the supplemental cushion 115. The thumb can remain extended until the cushion wrapping is complete. However, alternatively, the thumb can be relaxed once enough wrapping 111 has been done to secure the supplemental cushion 115, as depicted in both FIG. 4B and FIG. 5B. Then, the thumb can be relaxed as in FIG. 4A and FIG. 5A. Then, the sheath 113 is applied to the arm, typically by another wrapping motion, after which the sheath is hardened and set.

In some cases, as known to those skilled in the art, the medical practitioner will lift the exposed cushioning 111 up over the exposed edge of the sheath 113 and back over the top of the sheath 113. The cushioning 111 will then be attached to the sheath 113 during the process of sheath hardening (e.g., as the plaster, fiberglass or thermoplastic in the sheath hardens). This process is not depicted in FIG. 5A. The cushioning then provides additional protection for the patient's skin from rubbing against the rough edge of the sheath.

Figure 5A:
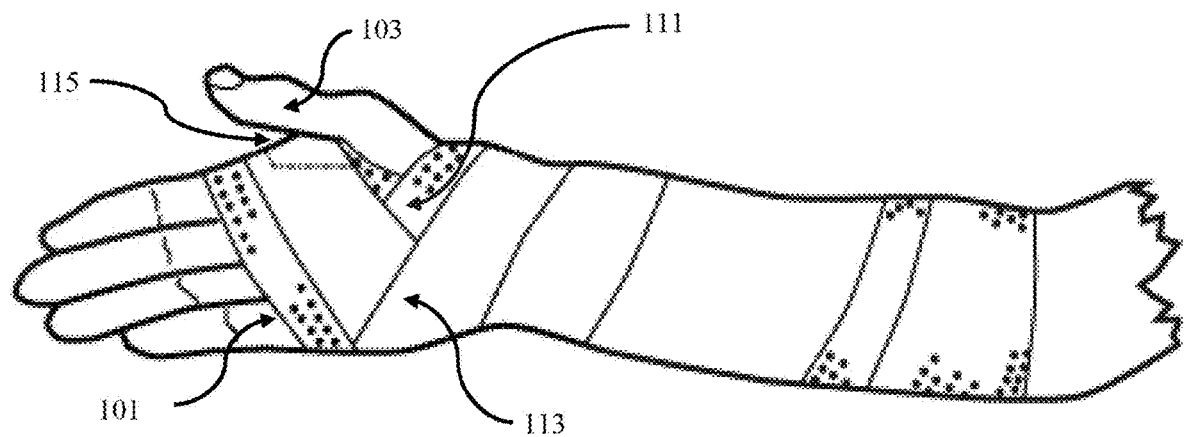
FIG. 5A shows a wrist cast formed on the right arm, wrist and hand of a patient, in accordance with an embodiment of the present invention, with the thumb in an at-rest position.
Figure 5B:
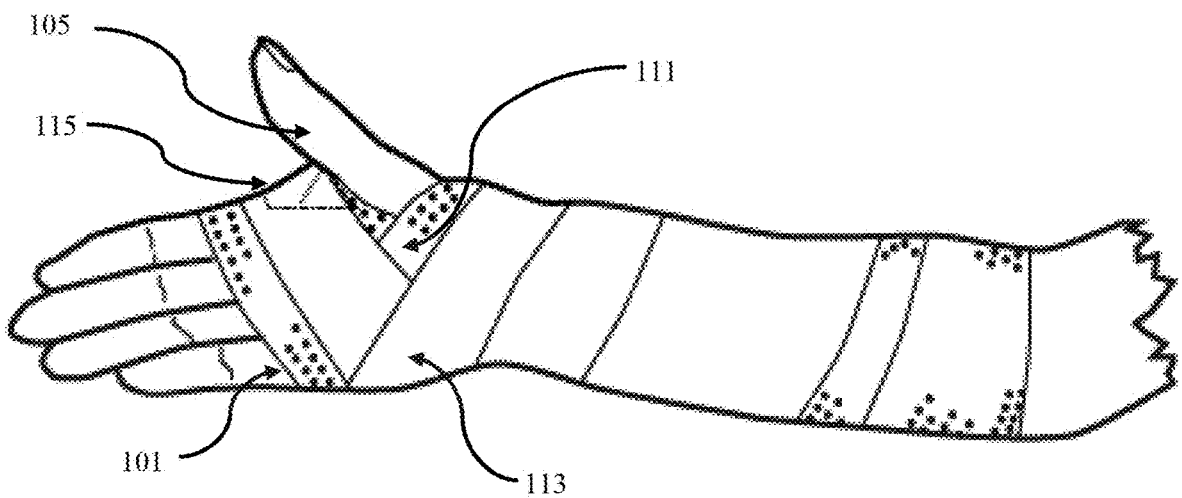
FIG. 5B shows a wrist cast formed on the right arm, wrist and hand of a patient, in accordance with an embodiment of the present invention, with the thumb in an extended position.

The supplemental cushion 115 in FIG. 5A is not visible because it is covered by padding 111 and sheath. However, the location of the supplemental cushion 115 is depicted by a dotted line. In FIG. 5B, again the supplemental cushion 115 is not visible, but is depicted as a dotted line. In addition, the webbing between thumb and forefinger (i.e., webbing 107 of FIG. 1B) is show by a dotted line, because the webbing is covered by the supplemental cushion 115.

Once the supplemental cushion is in place, there is a small gap created by the supplemental cushion 115, in its center between it and the palm of the hand 101. This gap is filled by the thenar space when the thumb is extended as in FIG. 5B, but remains empty when the thumb is relaxed as in FIG. 5A. This prevents the thenar space from rubbing against the cushion in an abrasive manner.

Consider now the alternative embodiment of the invention depicted in FIGS. 7A-7D, wherein the supplemental cushion is constructed of similar materials as the embodiment depicted in FIGS. 3A-3D and described above, but in a different shape. FIGS. 7A-7D show different views of an alternative embodiment of the supplemental cushion 715: orthogonal, frontal, side and top. As depicted, the cushion 715 is shaped like a tube, cut in half. It will sit flat on a planar surface, and provide a casing around an open space 717 which can accommodate the thenar space. More particularly, the cushion comprises a body 715 having a first, outer surface and an opposing second, inner surface. The inner surface defines a C-shaped cavity 717 configured to receive the thenar space therein. Alternative embodiments may be different sizes, different shapes, or have different cross-sections, as well as different shapes of the empty space 717.

Figure 9A:
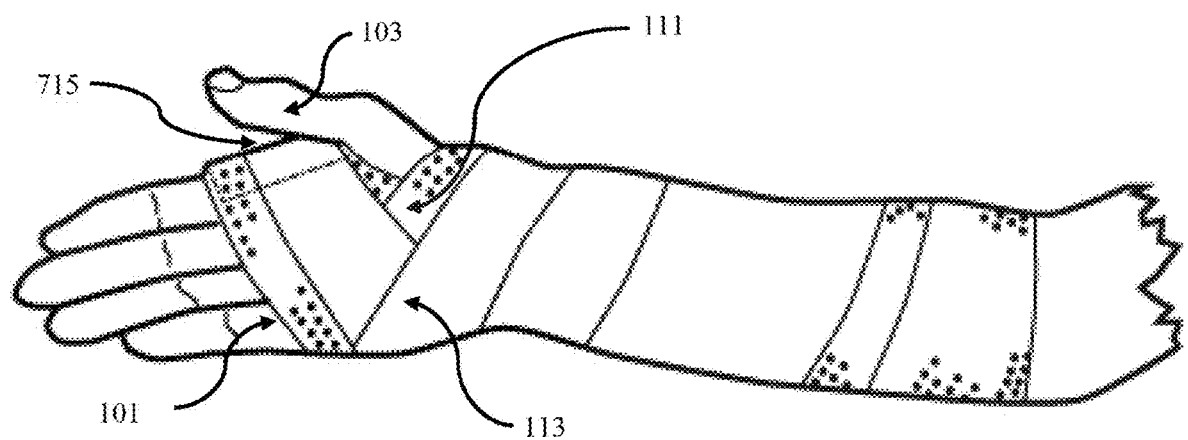
FIG. 9A shows a wrist cast including the cushion shown in FIGS. 7A-7D formed on the right arm, wrist and hand of a patient, in accordance with an embodiment of the present invention, with the thumb in an at-rest position and the cushion being completely covered by the porous cast padding and the rigid sheath.
Figure 9B:
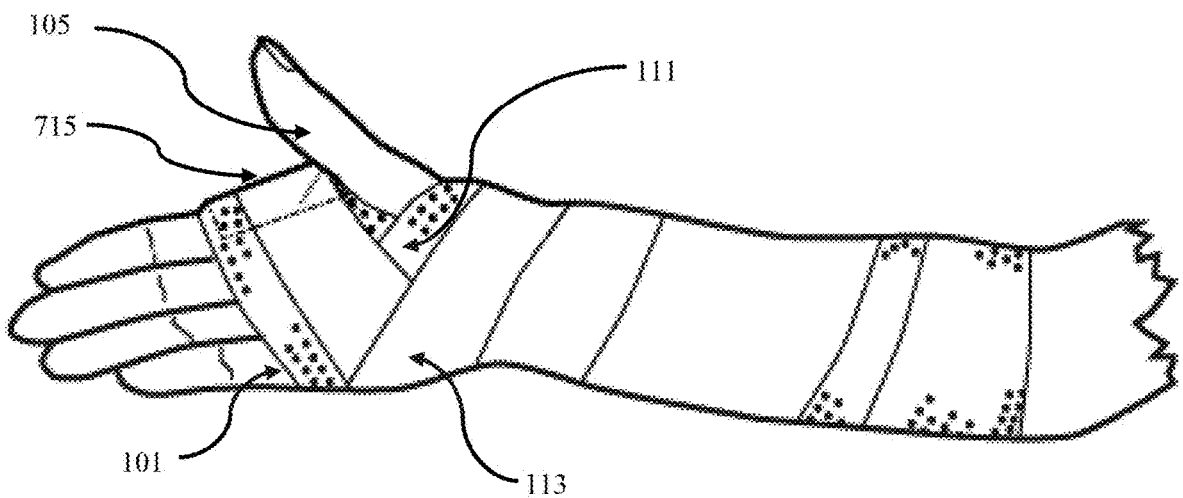
FIG. 9B shows a wrist cast including the cushion shown in FIGS. 7A-7D formed on the right arm, wrist and hand of a patient, in accordance with an embodiment of the present invention, with the thumb in an extended position and the cushion being completely covered by the porous cast padding and the rigid sheath.

As depicted in FIG. 9A and FIG. 9B, the alternative embodiment depicted in FIGS. 7A-7D fits on the hand in similar manner as the embodiment depicted in FIGS. 3A-3D, FIG. 4A, FIG. 4B, FIG. 5A, and FIG. 5B.

To apply the cast to the hand, the supplemental cushion 715 is first placed on the hand 101 over the thenar space, as depicted in FIG. 9B, with the thumb extended. Then, a cushion or padding 111 is begun to be wrapped around the hand 101 and the supplemental cushion 715. The thumb can remain extended until the cushion wrapping is complete. However, alternatively, the thumb can be relaxed once enough wrapping 111 has been done to secure the supplemental cushion 715, in FIG. 9B. Then, the thumb can be relaxed as in FIG. 9A. Finally, the sheath 113 is applied to the arm, typically by another wrapping motion, after which the sheath is hardened and set.

In some cases, as known to those skilled in the art, the medical practitioner will lift the exposed cushioning 111 up over the exposed edge of the sheath 113 and back over the top of the sheath 113. The cushioning 111 will then be attached to the sheath 113 during the process of sheath hardening (e.g., as the plaster, fiberglass or thermoplastic in the sheath hardens). This process is not depicted in FIG. 9A. The cushioning then provides additional protection for the patient's skin from rubbing against the rough edge of the sheath.

The supplemental cushion 715 in FIG. 9A is not visible because it is covered by padding 111 and sheath. However, the location of the supplemental cushion 115 is depicted by a dotted line. In FIG. 9B, again the supplemental cushion 115 is not visible, but is depicted by a dotted line. In addition, the webbing between thumb and forefinger (i.e., the webbing 107 of FIG. 1B) is show by a dotted line, because the webbing is covered by the supplemental cushion 715.

Once the supplemental cushion is in place, there is a small gap created by the supplemental cushion 715, in its center between it and the palm of the hand 101. This gap is filled by the thenar space when the thumb is extended as in FIG. 9B, but remains empty when the thumb is relaxed as in FIG. 9A. As such, the thenar space is prevented from rubbing against the cushion in an abrasive manner.

Figure 10A:
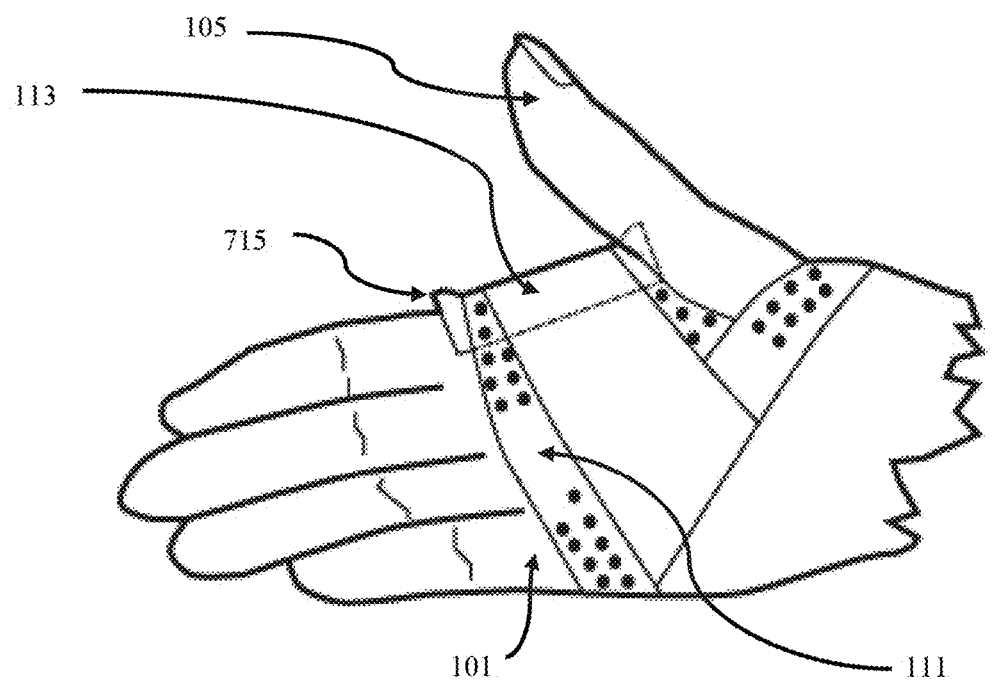
FIG. 10A shows a wrist cast including the cushion shown in FIGS. 7A-7D formed on the right arm, wrist and hand of a patient, in accordance with an embodiment of the present invention, with the thumb in an extended position and only a center portion of the cushion being covered by the porous cast padding and the rigid sheath, such that opposing distal ends of the cushion protrude beyond the porous cast padding and the rigid sheath.

An alternative method of applying the cast to the hand is depicted in FIG. 10A. In this method, the typical cushion or padding 111 and the typical sheath 113 do not fully cover the supplemental cushion 715. Instead, the typical cushion or padding 111 and the typical sheath 113 compress the center of the supplemental cushion 715 slightly, allowing the ends of the supplemental cushion to stand out a bit. This provides additional cushioning and protection for the thenar space and the palm of the patient's hand, with respect to the edge of the sheath material 113.

Figure 10B:
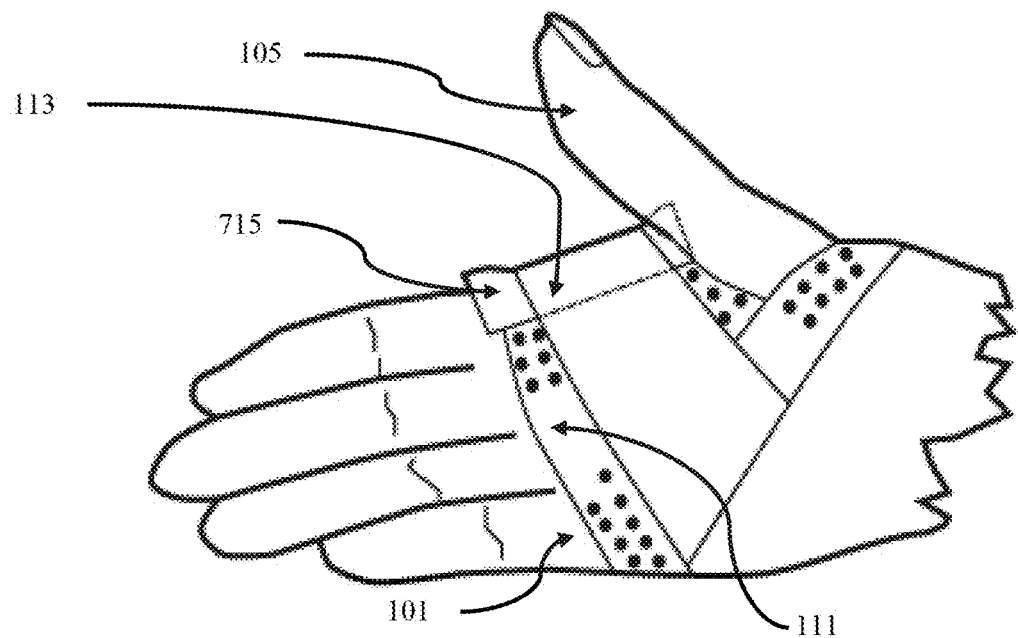
FIG. 10B shows a wrist cast including the cushion shown in FIGS. 7A-7D formed on the right arm, wrist and hand of a patient, in accordance with an embodiment of the present invention, with the thumb in an extended position, the cushion covering the porous cast padding and only a center portion of the cushion being covered by the rigid sheath, such that opposing distal ends of the cushion protrude beyond the rigid sheath.

An alternative method of applying the cast is depicted in FIG. 10B. In this method, the typical cushioning material 111 is applied first, the supplemental cushion 715 is applied second (i.e., over the cushioning material 111), and the typical sheath 113 is applied third. The typical sheath holds the supplemental cushion in place. As is evident to those skilled in the art of placing arms in casts, the previously described embodiment of the supplemental cushion depicted in FIGS. 3A-3D could also be placed on the hand after the typical cushioning and before the sheath material. The same applies to other alternative embodiments of the invention, such as those depicted in FIGS. 8A-8D and described below.

Referring again to FIG. 10A, in some cases, as known to those skilled in the art, the medical practitioner will lift the exposed cushioning 111 up over the exposed edge of the sheath 113, and back over the top of the sheath 113. Referring to FIG. 10B, in some cases, the medical practitioner will lift the exposed cushioning 111 up over the exposed edge of the sheath 113 and the supplemental cushion 715, and back over the top of the sheath 113. The cushioning 111 will then be attached to the sheath 113 during the process of sheath hardening (e.g., as the plaster, fiberglass or thermoplastic in the sheath hardens). This process is not depicted in the figures (FIG. 10A and FIG. 10B). The cushioning then provides additional protection for the patient's skin from rubbing against the rough edge of the sheath.

Another alternative embodiment of the invention is depicted in FIGS. 8A-8D, wherein the supplemental cushion in constructed of similar materials as the embodiment depicted in FIGS. 3A-3D and described above, but in a different shape. FIGS. 8A-8D show different views of an alternative embodiment of the supplemental cushion 815: orthogonal, frontal, side and top. As depicted, the cushion 815 is shaped like a spool for thread, but cut in half along the axis. It will sit flat on a planar surface, and provide a casing 815 around an open space 817 which can accommodate the thenar space. More particularly, the cushion comprises a body 815 having a first, outer surface and an opposing second, inner surface. The inner surface defines a C-shaped cavity 817 configured to receive the thenar space therein. Alternative embodiments may be different sizes, different shapes, or have different cross-sections, as well as different shapes of the empty space 817.

Figure 11A:
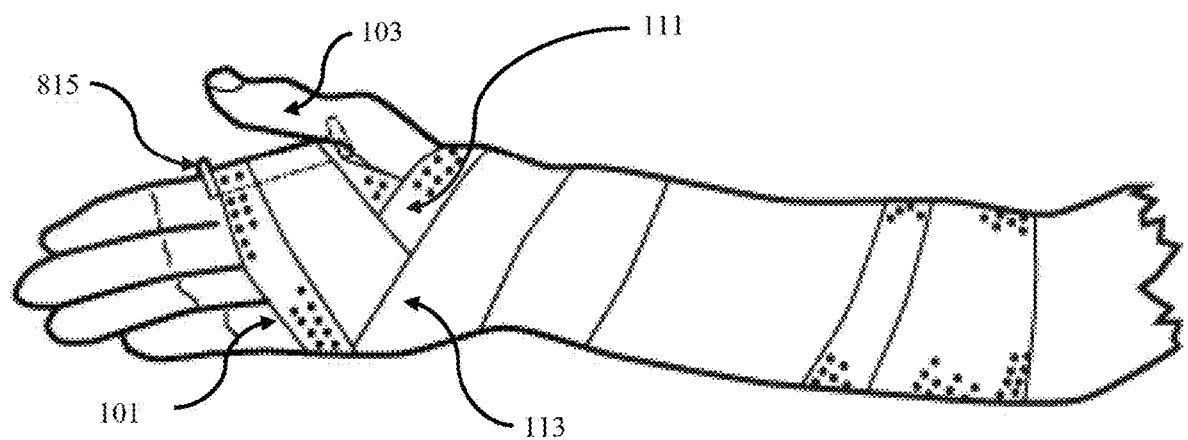
FIG. 11A shows a wrist cast including the cushion shown in FIGS. 8A-8D formed on the right arm, wrist and hand of a patient, in accordance with an embodiment of the present invention, with the thumb in an extended position and the cushion being covered and held in place by the porous cast padding and the rigid sheath.
Figure 11B:
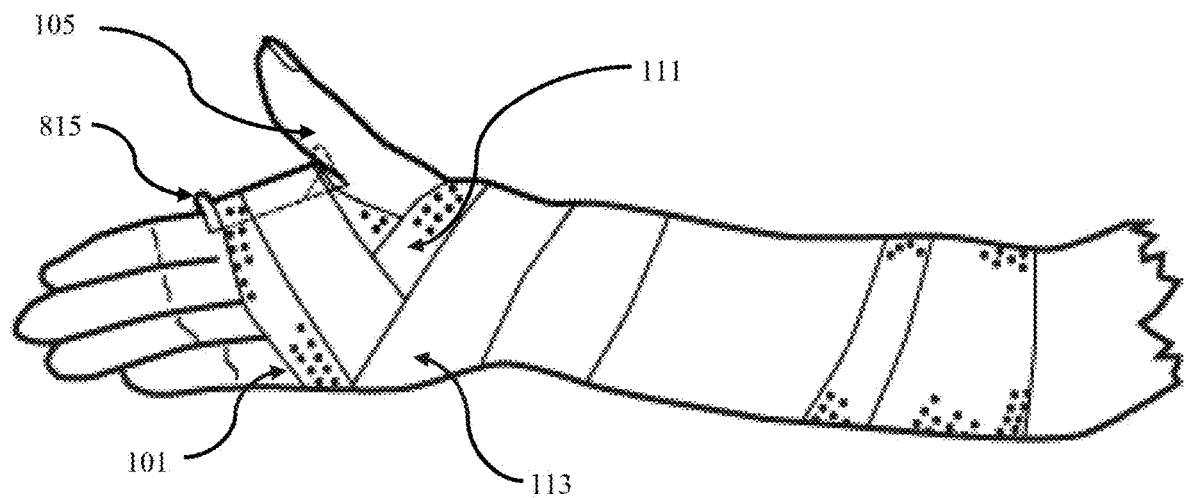
FIG. 11B shows a wrist cast including the cushion shown in FIGS. 8A-8D formed on the right arm, wrist and hand of a patient, in accordance with an embodiment of the present invention, with the thumb in an extended position, the cushion covering the porous cast padding and only the center portion of the cushion being covered by the rigid sheath.
Figure 12A:
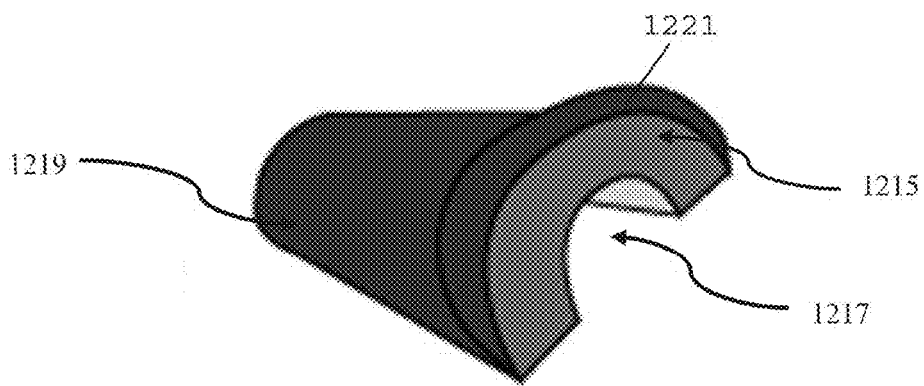
FIG. 12A is an orthogonal view of a cushion at least partially encased in or covered by a shell, in accordance with another embodiment of the present invention.
Figure 12B:
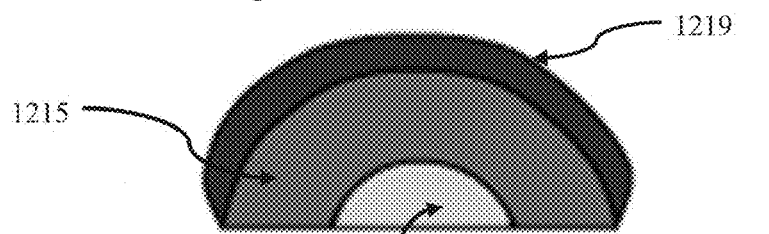
FIG. 12B is a front view of the cushion shown in FIG. 12A.
Figure 12C:
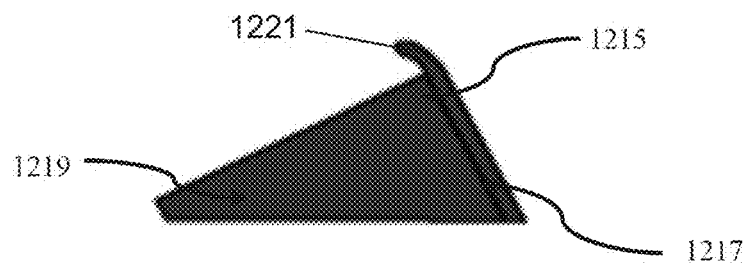
FIG. 12C is a side view of the cushion shown in FIG. 12A.
Figure 12D:
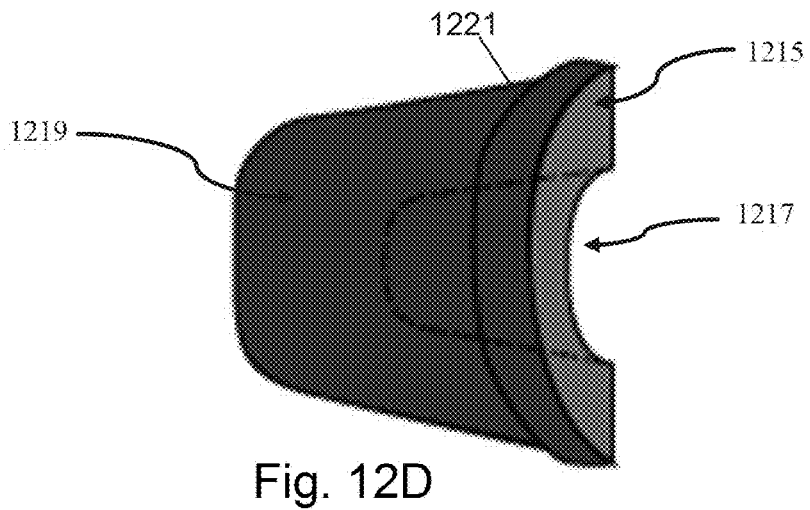
FIG. 12D is a top plan view of the cushion shown in FIG. 12A.

As depicted in FIG. 11A and FIG. 11B, the alternative embodiment of the supplemental cushion 815 depicted in FIGS. 8A-8D fits on the hand in similar manner as the preferred embodiment depicted in FIGS. 3A-3D, FIG. 4A, FIG. 4B, FIG. 5A, and FIG. 5B.

To apply the cast to the hand, the supplemental cushion 815 is first placed on the hand 101 over the thenar space, as depicted in FIG. 11B, with the thumb extended. Then, a cushion or padding 111 is begun to be wrapped around the hand 101 and the supplemental cushion 815. The thumb can remain extended until the cushion wrapping is complete. However, alternatively, the thumb can be relaxed once enough wrapping 111 has been done to secure the supplemental cushion 815 (in FIG. 11B). Then, the thumb can be relaxed as depicted in FIG. 11A. Then, the sheath 113 is applied to the arm, typically by another wrapping motion, after which the sheath is hardened and set.

The ends of the supplemental cushion 815 in FIG. 11A are exposed and visible, but the rest of the supplemental cushion is covered by padding 111 and sheath 113. In FIG. 11A, the position of the thumb is hiding one of the ends of the supplemental cushion. However, the location of the supplemental cushion 815 beneath the padding and sheath is depicted by a dotted line. In FIG. 11B, again only the ends of the supplemental cushion 815 can be seen (one is covered not visible, but is depicted as a dotted line). In addition, the webbing between thumb and forefinger (i.e., the webbing 107 of FIG. 1B) is depicted by a dotted line, because the webbing is covered by the supplemental cushion 815.

In some cases, as known to those skilled in the art, the medical practitioner will lift exposed cushioning 111 up over the exposed edge of the sheath 113 and back over the top of the sheath 113. The cushioning 111 will then be attached to the sheath 113 during the process of sheath hardening (e.g., as the plaster, fiberglass or thermoplastic in the sheath hardens). This process is not depicted in FIG. 11A. The cushioning then provides additional protection for the patient's skin from rubbing against the rough edge of the sheath.

Once the supplemental cushion is in place, there is a small gap created by the supplemental cushion 815, in its center between it and the palm of the hand 101. This gap is filled by the thenar space when the thumb is extended, as depicted in FIG. 11B, but remains empty when the thumb is relaxed, as depicted in FIG. 11A. This prevents the thenar space from rubbing against the cushion in an abrasive manner. In this embodiment, the ends of the supplemental cushion provide additional cushioning and protection for the thenar space and the palm of the patient's hand, especially with respect to the edge of the sheath material 113.

The embodiment depicted in FIGS. 8A-8D facilitates the additional cushioning offered by the ends of the invention, by incorporating the raised ends which guide the wrapping process. This additional cushioning can also be achieved via careful application by medical personnel of the cast wrapping materials to the embodiment depicted in FIGS. 7A-7D, as more fully detailed in FIGS. 10A and 10B. However, the embodiment depicted in FIGS. 8A-8D makes this extra cushioning automatic rather than relying upon the application skills of medical personnel.

Alternative embodiments of the supplemental cushion of the present invention employ different density of material, including plastic similar to that used in dental mouth guards, which are flexible, but not "spongy" or "cushy". This type of material may best be used in embodiments of the invention shaped as in FIGS. 8A-8D, or embodiments of the invention applied over the typical cushioning as in FIG. 10B.

In the situation, where the supplemental cushion is applied over the typical cushioning, as in FIG. 10B (see 111 in FIG. 10B), alternative embodiments of the supplemental cushion incorporate an adhesive on the surface thereof that comes in contact with the cushioning. The adhesive affixes the supplemental cushion to the cushioning while the limb and the supplemental cushion are wrapped in the strips of sheath material (e.g. 113 in FIG. 10B). The sheath material is what keeps the supplemental cushion in place during the healing process, but the adhesive (by affixing the supplemental cushion to cushioning 111) makes it easier for the medical practitioner to apply the sheath material 113, because the practitioner does not have to use his or her hand to hold the invention in place while doing the wrapping of the sheath material. In some embodiments, prior to incorporating the supplemental cushion into the cast, while the supplemental cushion is in storage, the adhesive is covered with a release strip. When the medical practitioner later applies the invention to the cushioning, the release strip is removed so that the adhesive can affix the supplemental cushion to the cushioning.

In an alternative embodiment, as shown in FIGS. 12A-15B, the upper surface of the supplemental cushion (that is, the surface closest to the cast sheath and farthest from the patient's skin) is at least partially, and more preferably entirely, covered by or encased in a shell, and more particularly a water-impervious shell. Specifically, referring to FIGS. 12A-12D, there is shown the casing of the supplemental cushion 1215, around an open space 1217 for the thenar webbing, and the shell 1219 which covers the supplemental cushion 1215. More particularly, the cushion comprises a body 1215 having a first, outer surface and an opposing second, inner surface. The inner surface defines a C-shaped cavity 1217 configured to receive the thenar space therein.

The supplemental cushion 1215 may be bonded to the shell 1219 by one of several methods known to those knowledgeable in the art. The shell 1219 may be a hard shell, composed of plastic or metal. Alternatively, the shell 1219 may be of a softer plastic, which is nonetheless still harder than the material of the supplemental cushion 1215. The shell 1219 performs several functions (based upon its specific configuration). This is the case even if the patient picks away at the supplemental cushion 1215, something not unknown among young and juvenile patients.

Figure 13A:
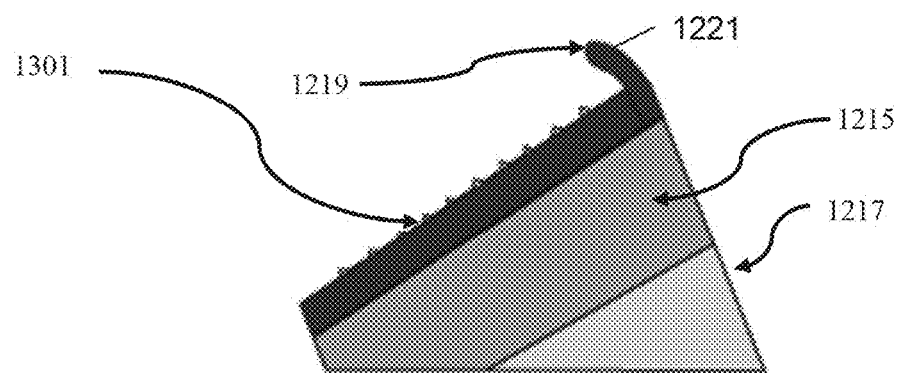
FIG. 13A shows a cut-away view of the cushion shown in FIGS. 12A-12D.

To better understand the configuration of supplemental cushion 1215 and hard shell 1219, see FIG. 13A. First, the shell 1219 maintains a not-rough (i.e., smooth) space in which the hand webbing can expand. Second, the shell 1219 helps guide the clinician as he or she winds the cast sheathing material around the wrist. Third, parts of the shell 1219 keep rough edges of the cast sheathing away from the patient's skin, thereby avoiding abrasion of the skin by the cast sheathing. In particular, in one embodiment, the shell 1219 may include a lip 1221 that projects from an edge of the shell 1219, so as to provide additional protection from the rough edge of the cast. Fourth, the part of the shell 1219 which may be touched by the patient's skin (especially as the patient moves his or her thumb, or flexes his or her palm) is preferably smooth and helps prevent abrasion and chaffing. Fifth, the upper surface of the shell 1219 which comes in contact with the cast sheathing is preferably roughened with tiny protrusions 1301 to help the cast sheathing (when hardened) keep the shell and its cushion in place in relationship to the patient's hand and thumb, as shown in FIG. 13A. In a preferred embodiment, the protrusions 1301 of the roughened surface are hard and "spikey". In an alternative embodiment, the protrusions are hooked and flexible like Velcro.

Alternatively, if the upper surface of the shell does not come in contact with the cast sheathing, but instead is intended to be covered by a layer of cast padding, the upper surface may be smooth and covered with adhesive as described above.

Figure 13B:
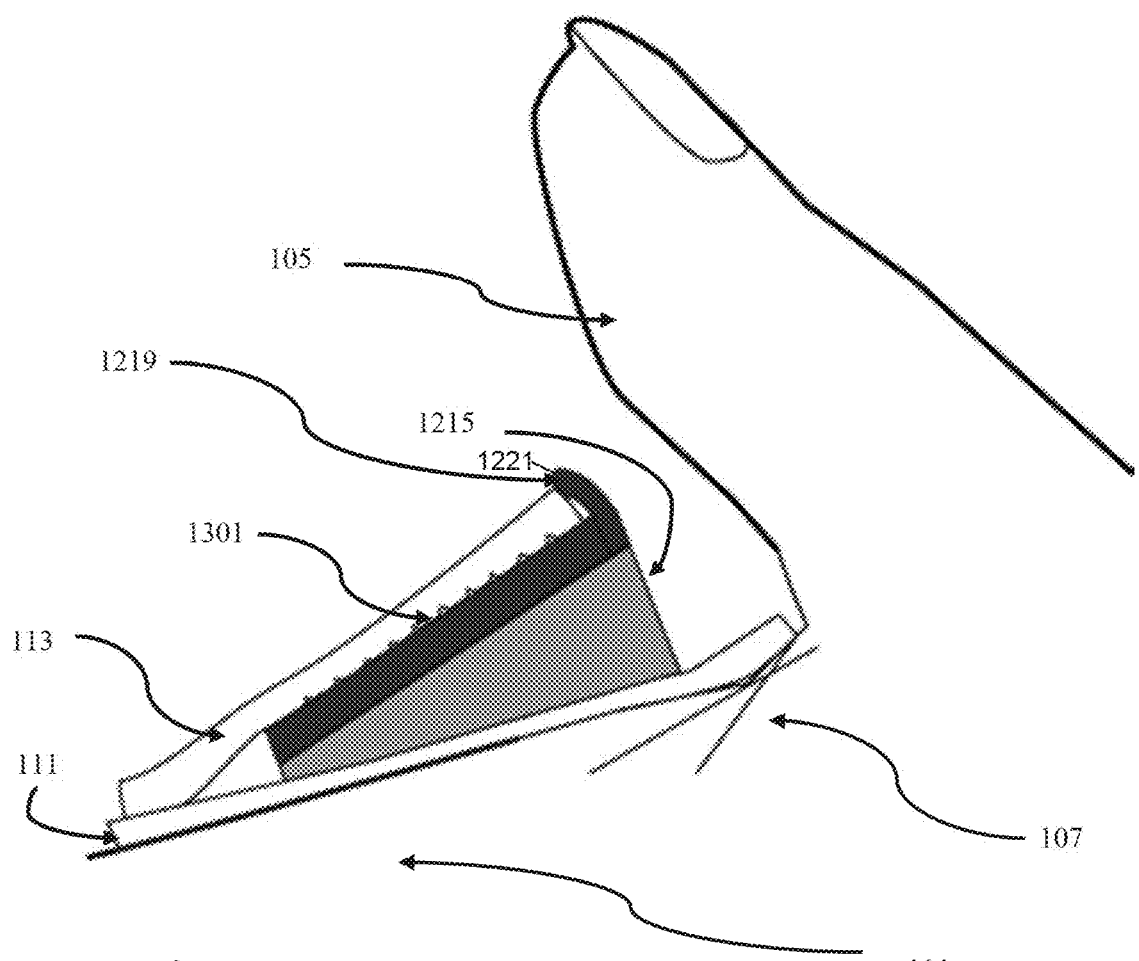
FIG. 13B shows a cut-away view of the cushion shown in FIGS. 12A-12D, after it has been used in the application of an orthopedic cast to a patient's right hand.
Figure 14A:
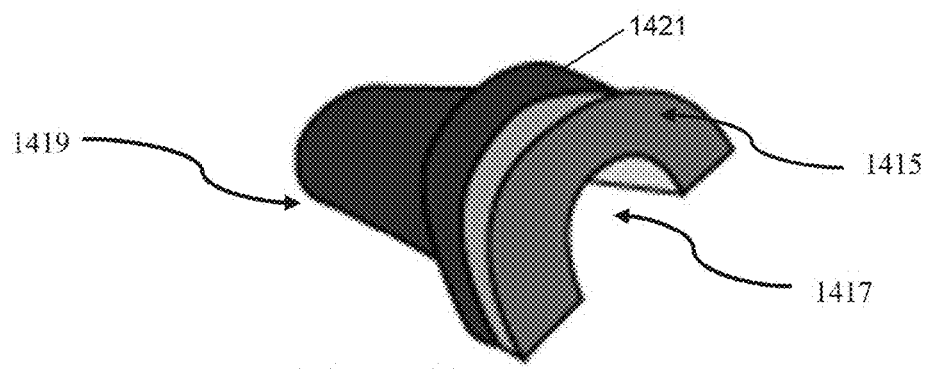
FIG. 14A is an orthogonal view of a cushion at least partially encased in or covered by a shell, in accordance with another embodiment of the present invention.
Figure 14B:
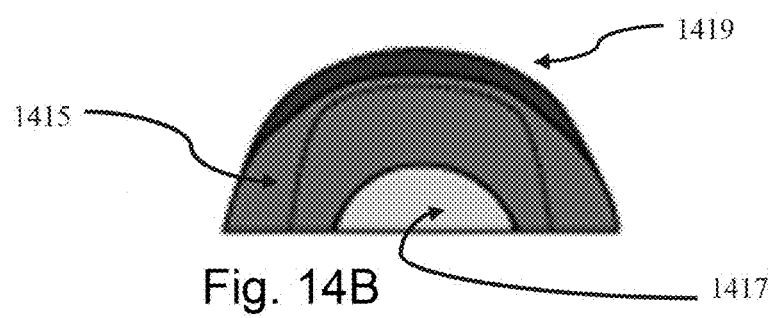
FIG. 14B is a front view of the cushion shown in FIG. 14A.
Figure 14C:
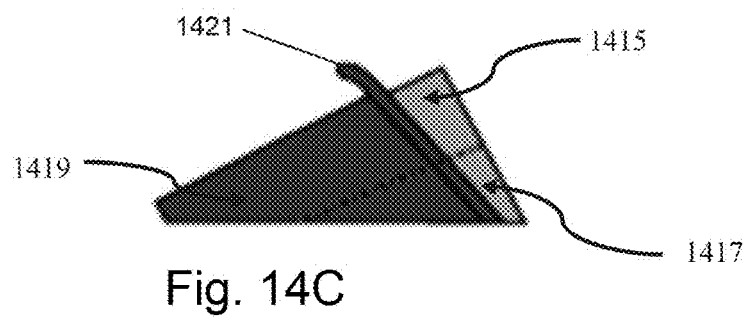
FIG. 14C is a side view of the cushion shown in FIG. 14A.
Figure 14D:
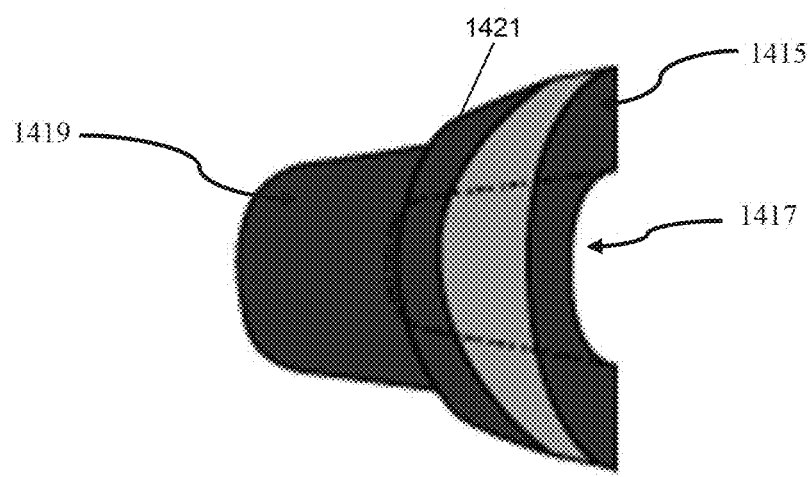
FIG. 14D is a top plan view of the cushion shown in FIG. 14A.

When placed on the patient's hand in conjunction with standard wrap padding and the casting sheath, the assembly of the present alternative embodiment looks very much like that of FIG. 5A and FIG. 5B. An enlarged, and more detailed "cut-away" view of the cushion with shell on a hand is shown in FIG. 13B. Referring to FIG. 13B, the cast padding 111 is first placed on the hand 101 with the thumb 105 extended and the thenar space 107 raised. Then, the inventive assembly (i.e., the supplemental cushion 1215 and the hard shell 1219 with the spikey protrusions 1301) is placed on top of the padding 111. Preferably, the supplemental cushion 1215 is compressed in places. Then, the cast sheathing 113 is applied on top of such an assembly. Preferably, the spikey protrusions 1301 anchor the inventive assembly into the cast sheathing, 113. This will prevent the inventive assembly from slipping out of the cast or out of position.

In an alternative embodiment, the hard shell does not completely cover the supplemental cushion. For example, referring to FIGS. 14A-14D, there is shown the casing of the supplemental cushion 1415 around an open space 1417 for the thenar webbing and the hard shell 1419 which covers part of the cushion. More particularly, the cushion comprises a body 1415 having a first, outer surface and an opposing second, inner surface. The inner surface defines a C-shaped cavity 1417 configured to receive the thenar space therein. To better understand the configuration of supplemental cushion 1415 and hard shell 1419, see FIG. 15A.

Figure 15A:
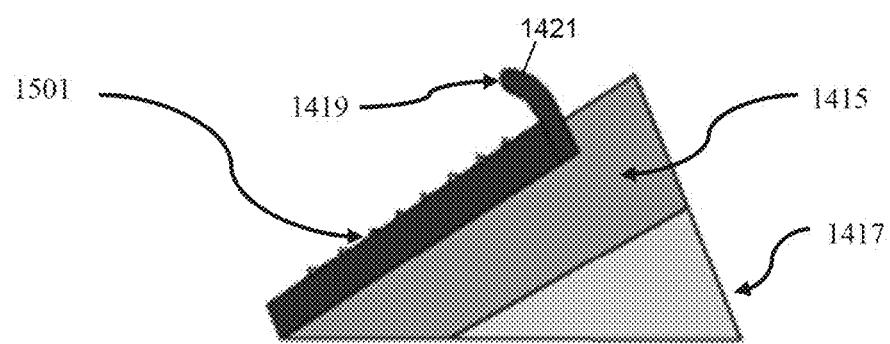
FIG. 15A shows a cut-away view of the cushion shown in FIGS. 14A-14D.
Figure 15B:
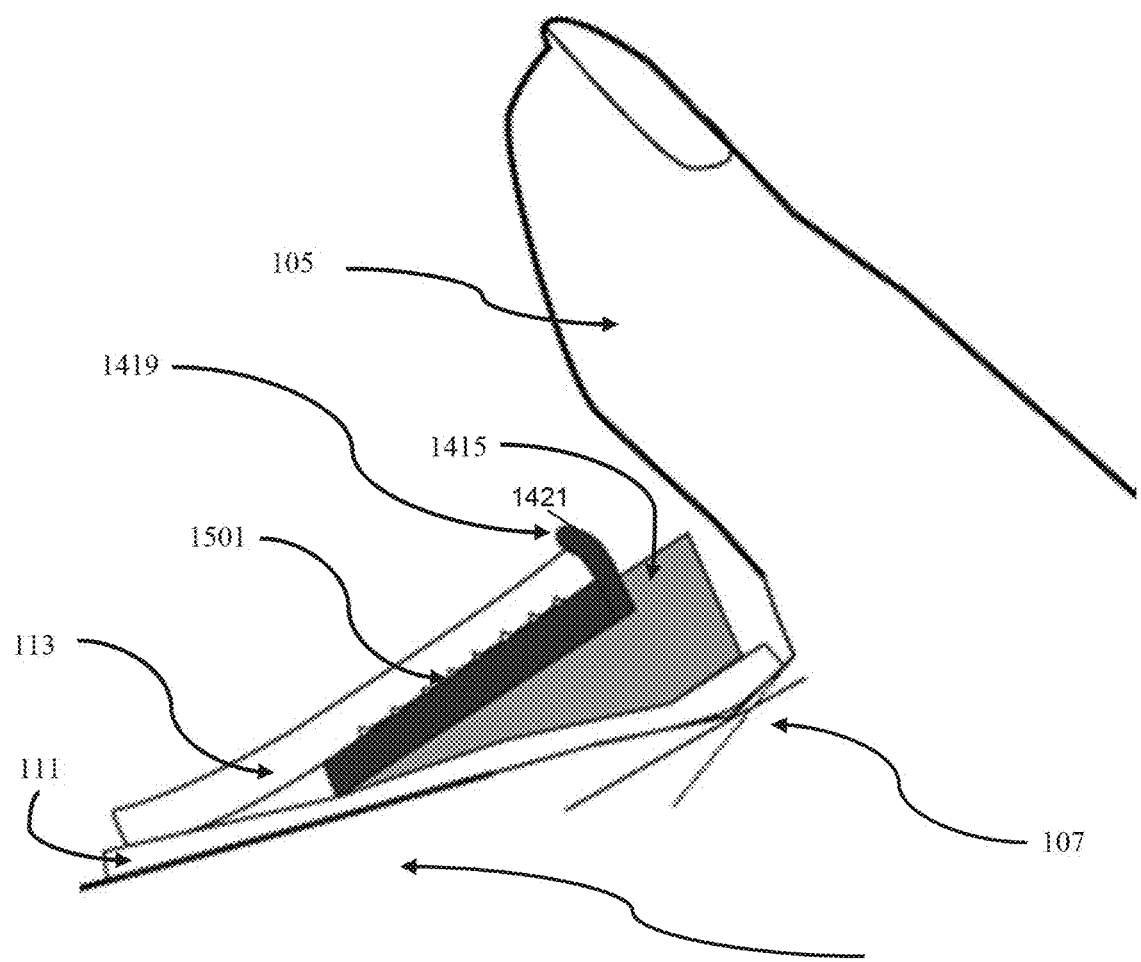
FIG. 15B shows a cut-away view of the cushion shown in FIGS. 14A-14D, after it has been used in the application of an orthopedic cast to a patient's right hand.

When the assembly is placed on the patient's hand in conjunction with standard wrap padding and the casting sheath, the assembly looks very much like that of FIG. 5A and FIG. 5B. An enlarged, and more detailed "cut-away" view of the cushion with shell on a hand is shown in FIG. 15B. The cast padding 111 is first placed on the hand 101 with the thumb 105 extended and the thenar space 107 raised. Then, the inventive assembly (i.e., the supplemental cushion 1415 and the hard shell 1419 with the spikey protrusions 1501 and lip 1421) is placed on top of the padding 111. Preferably, the supplemental cushion 1415 is compressed in places. Then the cast sheathing 113 is applied on top of such an assembly. Preferably, the spikey protrusions 1501 anchor the inventive assembly into the cast sheathing 113. This will prevent the inventive assembly from slipping out of the cast or out of position.

In alternative embodiments, the shell 1219, 1419 may be used without a cushion to create a space for the thenar webbing.

The supplemental cushion of the present invention is flexible and resilient and sufficiently thick so as to provide significant cushioning. The supplemental cushion is also preferably designed to be applied in line with the index finger, and can be placed between the patient's skin and a stockinette (i.e., the bandage/cushion), or between the stockinette and sheath. It will also be understood that no adhesive is needed to attach the supplemental cushion to the sheath or stockinette (i.e., the bandage/cushion). Embodiments of the supplemental cushion also, as described above, creates an empty space (or cushioning material) for the skin webbing to expand into when the thumb is flexed.

The supplemental cushion of the present invention is economical to construct and requires few steps to apply. It is thus efficient to use, saving significant labor for the medical personnel applying the cast, and reducing the cost of the overall procedure.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A cushion for use in an orthopedic cast, the cushion comprising a body having a first, outer surface and an opposing second, inner surface, the body of the cushion being formed of a compressible material with structural integrity to retain shape of the body-,
    wherein in a first position, prior to application of the cushion on a patient's hand, the inner surface defines a cavity configured to receive the thenar space of the patient's hand, and
    wherein in a second position, after application of the cushion on the patient's hand, the cavity is configured to be empty when a thumb of the patient is relaxed and is configured to receive the thenar space of the patient's hand when the thumb is extended such that the thenar space is not crushed.

2. The cushion according to claim 1, wherein the cushion comprises a closed-cell synthetic material.

3. The cushion according to claim 2, wherein the closed-cell synthetic material of the cushion is water and air impermeable.

4. The cushion according to claim 2, wherein the closed-cell synthetic material of the cushion is non-absorbent.

5. The cushion according to claim 2, wherein the closed-cell synthetic material of the cushion is thermal foam closed-cell polyethylene.

6. The cushion according to claim 1, wherein the cushion is formed of flexible elastomeric foam.

7. The cushion according to claim 1, wherein the cavity is C-shaped.

8. The cushion according to claim 1, wherein at least one distal end of the cushion includes a lip that protrudes outwardly beyond a remainder of the body of the cushion.

9. The cushion according to claim 1, wherein the outer surface of the cushion has a smooth finish.

10. The cushion according to claim 1, wherein the outer surface of the cushion is roughened.

11. The cushion according to claim 1, wherein at least a portion of the outer surface of the cushion is covered by a shell.

12. The cushion according to claim 11, wherein the shell is water-impervious.

13. The cushion according to claim 11, wherein the shell is made of a material that is more rigid than that of the body of the cushion.

14. The cushion according to claim 11, wherein at least one distal end of the shell includes a lip that protrudes outwardly beyond a remainder of a body of the shell.

15. The cushion according to claim 1, wherein the body comprises at least one material selected from the group consisting of an anti-microbial material, an anti-fungal ingredient and an anti-bacterial ingredient.

16. An orthopedic cast for encasing an upper extremity of a patient, the orthopedic cast comprising:
    a cushion comprising a body having a first, outer surface and an opposing second, inner surface, the body of the cushion being formed of a compressible material with structural integrity to retain shape of the body;
    a porous cast padding; and
    a sheath formed of a hardenable material,
        wherein in a first position, prior to application of the cushion on a patient's hand, the inner surface defines a cavity configured to receive the thenar space of the patient's hand and
        wherein in a second position, after application of the cushion on the patient's hand, the cavity is configured to be empty when a thumb of the patient is relaxed and is configured to receive the thenar space of the patient's hand when the thumb is extended such that the thenar space is not crushed.

17. The orthopedic cast according to claim 16, wherein the cushion is completely covered by the porous cast padding and the sheath.

18. The orthopedic cast according to claim 16, wherein the porous cast padding and the sheath are arranged so as to cover and compress a center portion of the cushion, such that distal ends of the cushion are exposed and protrude outwardly from the porous cast padding and the sheath.

19. The orthopedic cast according to claim 16, wherein the cushion is positioned between the porous cast padding and the sheath.

20. A method of forming a cast to encase a portion of a patient's upper extremity, the method comprising:
    obtaining a cushion comprising a body having a first, outer surface and an opposing second, inner surface, the cushion being formed of a compressible material with structural integrity to retain shape of the body wherein in a first position, prior to application of the cushion on a patient's hand, the inner surface defines a cavity configured to receive the thenar space of the patient's hand;
    applying the cushion to cover the thenar space of the patient's hand with the thumb of the patient's hand being extended, such that the thenar space is received within the cavity of the cushion, wherein in a second position, after application of the cushion on the patient's hand, the cavity is configured to be empty when the thumb of the patient is relaxed and is configured to receive the thenar space of the patient's hand when the thumb is extended such that the thenar space is not crushed; and
    applying a sheath made of a hardenable material over the cushion and allowing the material to harden in order to form the cast.

21. The method according to claim 20, further comprising wrapping a porous cast padding around the cushion and the portion of the upper extremity prior to applying the sheath, such that the cushion is held in place against the patient's hand.

22. The method according to claim 20, further comprising wrapping a porous cast padding around the portion of the upper extremity prior to applying the cushion, such that the cushion is positioned between the porous cast padding and the sheath.

* * * * *

UNITED STATES PATENT AND TRADEMARK OFFICE
CERTIFICATE OF CORRECTION

PATENT NO. : 11,278,438 B2
APPLICATION NO. : 16/102853
DATED : March 22, 2022
INVENTOR(S) : Benjamin Slotznick et al.

It is certified that error appears in the above-identified patent and that said Letters Patent is hereby corrected as shown below:

In the Specification

Column 4, Line 26: change "extended" to "relaxed"

Signed and Sealed this
Twenty-eighth Day of June, 2022

*Katherine Kelly Vidal*

Katherine Kelly Vidal
*Director of the United States Patent and Trademark Office*